United States Patent [19]

Henry

[11] 4,240,110

[45] Dec. 16, 1980

[54] INSPECTION OF ELONGATED MATERIAL

[75] Inventor: James W. Henry, Kingsport, Tenn.

[73] Assignee: Eastman Kodak Company, Rochester, N.Y.

[21] Appl. No.: 943,510

[22] Filed: Sep. 18, 1978

[51] Int. Cl.³ ............................................. H04N 7/18
[52] U.S. Cl. ................................... 358/107; 358/93; 358/106; 235/92 PD
[58] Field of Search .................. 358/93, 107, 106; 235/92 PD

[56] References Cited

U.S. PATENT DOCUMENTS

| | | | |
|---|---|---|---|
| 3,868,478 | 2/1975 | Zeenkov | 358/93 |
| 3,873,812 | 3/1975 | Stein | 358/93 |
| 4,140,898 | 2/1979 | Gasser | 235/92 PD |

*Primary Examiner*—Howard W. Britton

*Attorney, Agent, or Firm*—Daniel B. Reece, III; John F. Stevens

[57] ABSTRACT

Apparatus and method are described for inspecting elongated material such as strands, sheets, bundles or webs for the presence of surface irregularities, count of irregularities within a given length and angle of irregularities such as in the case of crimped fiber. A light source is used to form light areas and shadowed areas of the elongated material. A television camera produces a video signal of the light and shadowed areas and such signal is electronically analyzed with respect to number of alternating light and dark areas within a given length, and the relative widths of such light and dark areas, from which information can be obtained to confirm presence of irregularities, count or frequency, and angle. A filter is disclosed for removing relatively low frequency signals caused by unintentional shadowing from the useful signals so that the accuracy of the apparatus is improved.

10 Claims, 10 Drawing Figures

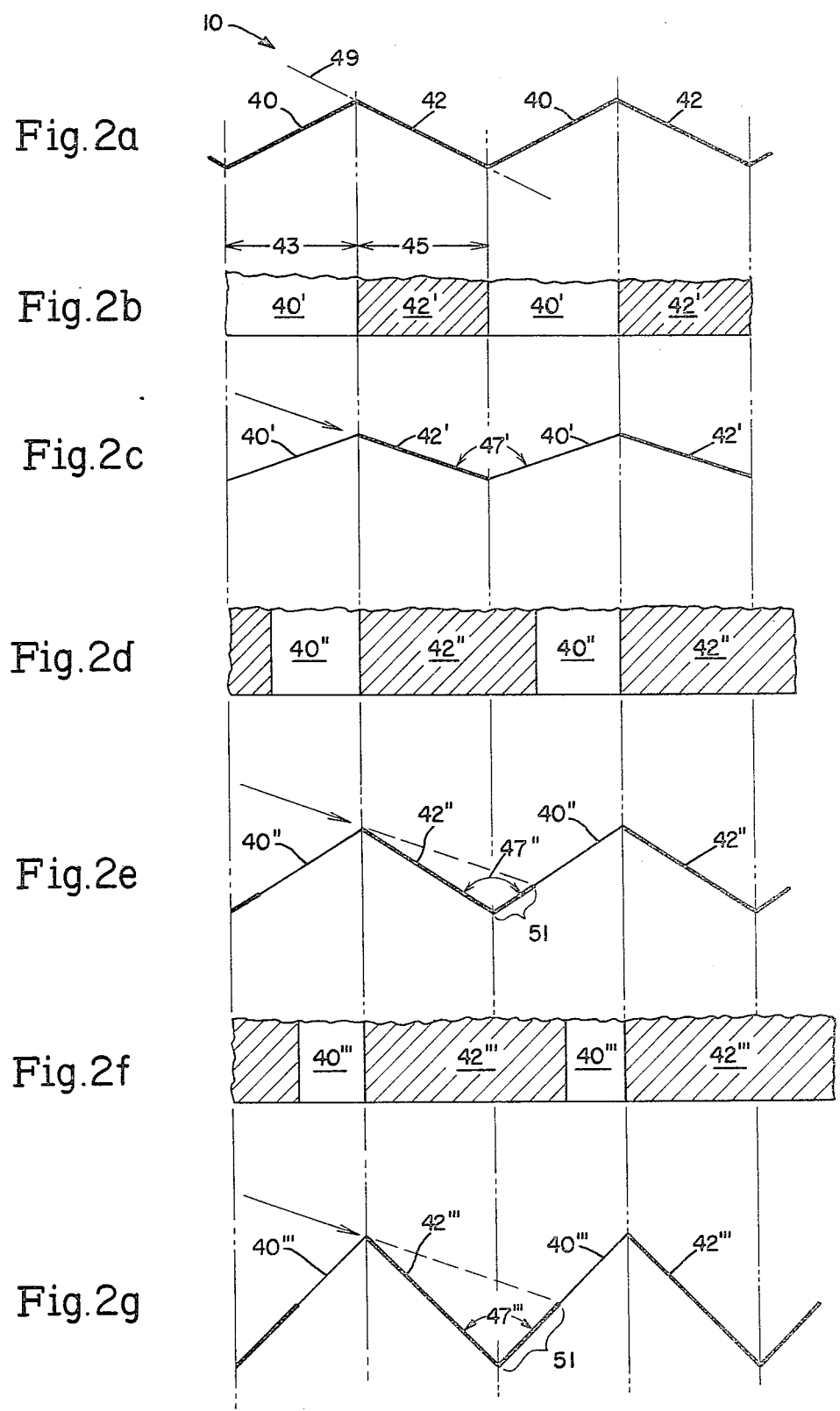

INSPECTION OF ELONGATED MATERIAL

BACKGROUND OF THE INVENTION

1. Field of the Invention

This invention relates generally to apparatus and method for inspection of elongated material. More specifically, this invention relates to apparatus and method for inspecting elongated material such as strands, sheets, bundles or webs for the presence of surface irregularities, count of irregularities within a given length, and angle of irregularities such as in the case of crimped fiber. Data obtained from such inspection may be used for quality control purposes.

This invention is particularly useful in monitoring production lines where continuous lengths of sheet or fibrous material is produced. Although various inspection uses will be apparent to those skilled in the art the present invention will be described herein mainly in reference to the production of fiber tow which has been evenly crimped. Such fiber tow, e.g., cellulose acetate filter tow, is mechanically crimped for various reasons known to those skilled in the art. Due to factors beyond the control of the machines or their operators, however, sometimes there are lengths of the tow where crimp does not appear, or the frequency (count per unit length) or the degree of crimp is off specification. Such faults can be caused by improper mechanical adjustments or improper condition of the material being crimped. Absence of crimp, incorrect crimp pitch, or incorrect crimp angle in the material results in rejection of the material by customers and subsequent heavy losses to the manufacturer because of waste. The present invention provides a method and apparatus whereby such crimp may be continuously monitored, and if faulty conditions are detected, the appropriate steps can be taken before substantial loss results. Furthermore, such detection systems can be designed so that a plurality of production lines may be alternately monitored from a central location.

In accordance with the present invention, apparatus including a television camera and associated stroboscopic light are provided for producing a video signal from a portion of continuous material having surface variations, to electronically obtain useful information from such material. As described herein, the stroboscopic light is positioned at an angle such that a pattern of light and dark (shadowed) areas or strips result on the material. The video signal produced is passed through a system which uses the light and dark areas to obtain information relative to the physical properties of the material. In practice, the material is often advancing along a path which may fluctuate slightly in various directions. Such fluctuations may be caused by a number of different conditions, such as nonuniform tension on the material, variations in weight, etc. The fluctuations may interfere with obtaining the useful information, such as by giving false signals. The false signals result from unintentional shadowing of areas of the material being monitored, and produce relatively low frequency video signals. The apparatus and method herein described filters such signals from the useful signals so that much more accurate information is obtained.

2. Description of the Prior Art

Various electronic systems are presently known for detecting defects in continuous lengths of material. For example, U.S. Pat. No. 3,584,225 relates to a yarn inspection device which uses optical devices and electronic circuitry to detect defects in yarn. U.S. Pat. No. 3,114,797 relates to a television system for detecting differences or changes in shape, size, color, intensity or texture. Such differences or changes are detected by comparing a scene at one instant with an image produced from the same scene after a time delay. U.S. Pat. No. 3,700,903 relates to detection systems wherein a coherent light beam is used to scan the surface of an object in a repetitive pattern. An output signal is produced by light reflected from the object for determining characteristics of the surface of the object. The present invention provides apparatus and method for continuously monitoring continuous lengths of material, for detecting surface irregularities, obtaining data from such irregularities, and converting such data into useful information. While the prior art shows the detection of surface defects or differences, this is often not sufficient for adequate quality control. Applicant's invention provides for obtaining additional useful information from irregularities such as count and shape.

SUMMARY OF THE INVENTION

The present invention provides apparatus and a method for obtaining information from an advancing continuous length of material comprising (A) a television camera positioned such that its field of view is a portion of the advancing elongated material, (B) a stroboscopic light positioned adjacent the path of the elongated material such as to illuminate the elongated material at an angle to cause a pattern of light and shadowed areas, (C) means synchronizing the television camera and stroboscopic light such that a television frame is initiated during an illumination, and a video signal is formed of the illuminated material, (D) means for filtering low frequency signal components from the composite video signal caused by different illumination intensities on relatively large areas of the elongated material including
  (a) a first amplifier
  (b) means for feeding the composite signal into an input terminal of the first amplifier,
  (c) means electrically connecting the output terminal of the first amplifier to the input terminal of a second amplifier,
  (d) a capacitor circuit connecting the input and output terminals of the second amplifier, the capacitor circuit and the second amplifier being operable to integrate the input signal to the second amplifier as a function of time, the integration rate being too slow to follow the high frequency elements but sufficiently fast to follow the low frequency elements,
  (e) means electrically connecting the output terminal of the second amplifier to the input terminal of a third amplifier having unity amplification and polarity reversal with respect to the second amplifier,
  (f) means electrically connecting the output terminal of the third amplifier to an input terminal of the first amplifier, whereby the output from the first amplifier is the difference between the integrated signal output of the first amplifier and the combined high and low frequency components, and
  (g) means electrically connecting the output terminal of the first amplifier with the input terminal of a fourth amplifier, whereby only the high frequency elements are amplified, (E) means for further processing the video signal to obtain said desired information relative to surface irregularities.

Such method and apparatus provide a convenient and reliable means for monitoring production lines to obtain physical data therefrom which can be electronically processed as a quality control measure.

BRIEF DESCRIPTION OF THE DRAWINGS

FIG. 2a is an elevation views of crimped fiber tow. FIGS. 2b through 2g are elevation and plan view, shown diagrammatically, of fiber tow crimped at different angles, and the direction of light beam from the stroboscope.

DETAILED DESCRIPTION OF THE INVENTION

To insure uniformity of the tow, it is necessary to maintain the presence of crimp, a particular crimp count or frequency for a given length of tow, and/or crimp angle. The present invention provides a method and apparatus for detecting absences of crimp in the tow, the number of crimps per unit length, and the crimp angle.

Figure 1:
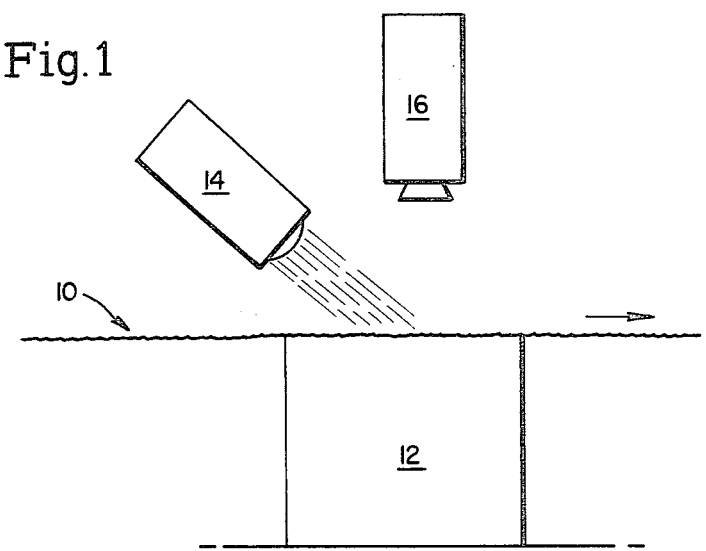
FIG. 1 is a partial schematic elevation view illustrating a preferred arrangement of elongated material, television camera, and stroboscope.

Referring to FIG. 1, irregular filamentary material, e.g., a continuous band of crimped fiber tow 10, is fed over support 12 in the direction indicated. For the sake of simplicity, the filamentary material will be hereinafter referred to as tow. The tow generally moves at a rapid rate, for example, about 20 feet per second, but, of course, the speed may be much slower or much faster. Support 12 may be placed in a convenient position anywhere along the path of the crimped tow in various conventional operations well known in the art, or may be a separate inspection operation.

Stroboscope 14 is positioned adjacent the band of tow 10 so as to illuminate a portion of tow 10 as it passes over support 12. Stroboscope 14 is positioned at an angle relative to the direction of movement of tow 10 as shown in FIG. 1 to create a pattern of alternate light and dark strips on the tow as described hereinafter. Television camera 16 is placed in close proximity to stroboscope 14 in a manner such that the pattern of light and dark strips created by the light on the crimped tow will be in its field of view. Preferably, camera 16 is aimed substantially directly at a generally linear section of the tow. Also, the stroboscope 14 is directed towards the tow at an angle such that the generally parallel rays of light are substantially parallel to the tow sections 42 at the maximum anticipated crimp angle.

Figure 3:
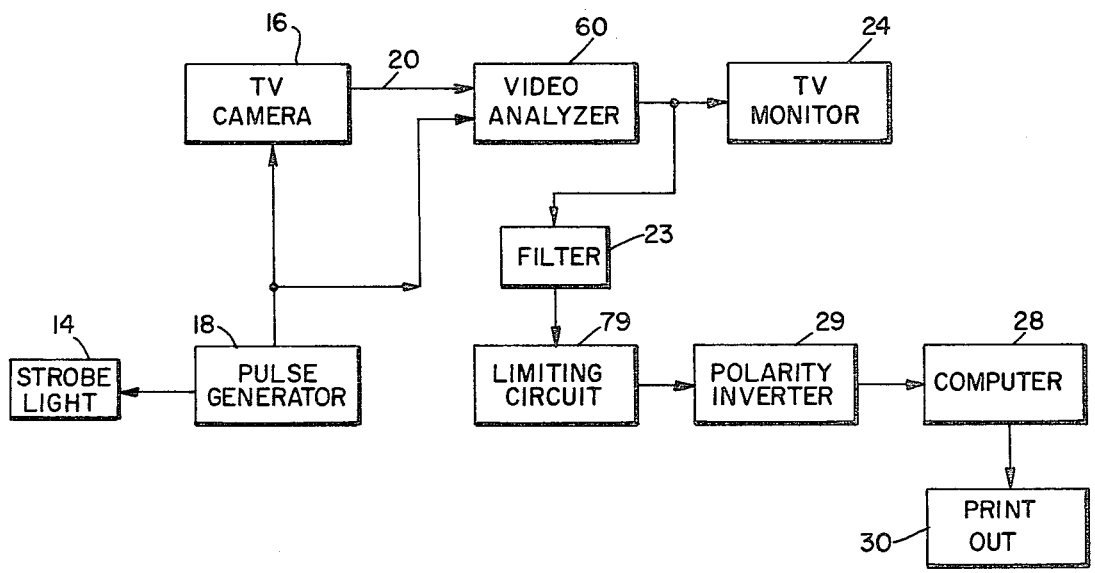
FIG. 3 is a diagram of the electrical components used in this invention.

As shown in the diagram of FIG. 3, the television camera 16, the synchronization pulse of which is controlled by the pulse generator 18, feeds its video signal into a video analyzer system 60. The electrical signal from the video analyzer is fed to a television monitor 24 and preferably to a filter 23 prior to being fed to a limiting circuit 79 which reshapes the waveform, then through a polarity inverter 29 which feeds square wave impulses into computer 28, which is preferably connected to print-out machine 30. Coordination of television camera 16 and stroboscope 14 is maintained by pulse generator 18.

FIGS. 2b and 2c are diagrammatic sketches illustrating in somewhat simplified form the section of tow shown in FIG. 2a. FIG. 2b illustrates the principals involved in creating light and dark strips on a section of tow by directing a beam of light at an angle to the crimp. Preferably the beam of light is collimated in at least one plane, i.e., the plane of the paper. Light from the direction illustrated by the arrow creates light strips 40 and dark strips or shadows 42 on the crimped tow 10. These alternating light strips 40 and dark strips 42 are detected by television camera 10 and appear in the video signal developed by camera 10. Also, the width 43 and 45 of the strips which appear in FIG. 2c, for a predetermined crimp size, is a function of crimp angle 47 which can be determined mathematically by computer by well known means.

In practice, crimped tow normally will not have sharply defined angles and absolutely flat sections from the angles. Actually, the tow may appear somewhat wavy as shown in FIG. 2a. The light would thus be directed substantially parallel the side 42 sloping away from the light, i.e., parallel to a line 49 which is tangent to the bends in the tow.

FIGS. 2b through 2g illustrate the relationship between the width of the strips and the crimp angle. FIGS. 2b and 2c illustrate the light rays (arrow) parallel to side 42' at the maximum anticipated crimp angle 47'. FIGS. 2d and 2e illustrate a slightly decreased angle 47" at which time the light strips 40" get smaller and dark areas 42" get larger because of the shadow 51 cast on side 40'. In FIGS. 2f and 2g, angle 47"' has decreased even more, casting a longer shadow 51, thus making the light strips 40"' even smaller and the dark strips 42"' even larger. As will be apparent to those skilled in the art, a direct relationship exists between the number of strips for a given length of tow and crimp count, and a direct relationship exists between the width of dark strip relative to width of light strip and the crimp angle. Such relationships may be programmed on a computer for obtaining numerical data by those skilled in the art.

The number of alternating light strips and shadow strips per unit length, and the relative width of such strips is therefore transformed into a video signal for analysis.

The video signal from the television camera is processed by a system shown diagrammatically in FIG. 3. The television camera 16 is synchronized as to frame rate and scanning rate by synchronization generator 18. The vertical synchronization pulse from the generator is used to trigger stroboscopic light source so that at the beginning of each field scan a pulse of light is triggered to light the tow band. The image reflected through the camera lens to the sensitive vidicon tube is stored in the tube and is read out by the scanning electron beam which generates the video signal. Because of the extremely short pulse of light, the image stored on the tube is not blurred due to movement of the tow. The video signal from the camera 16 is transferred to a video analyzer 60 where a selected group of luminance signals along a line perpendicular to the scanning lines of the picture are analyzed and presented as a slow scan video signal. The composite picture of the full television frame with an added graphic display of the slow scan video signal is shown on a television monitor 24. The slow-scan television signal (e.g., about 525 lines and about 30 frames per second) is fed to a limiting circuit 79 and converted to a square wave representation of the signal in which frequency is converted to pulse rate and wave length to pulse duty cycle. These pulses are analyzed for frequency and duty cycle by computer 28 which calculates the crimp frequency (or count) and crimp angle, and presents it as a printout on printer 30.

Figure 4:
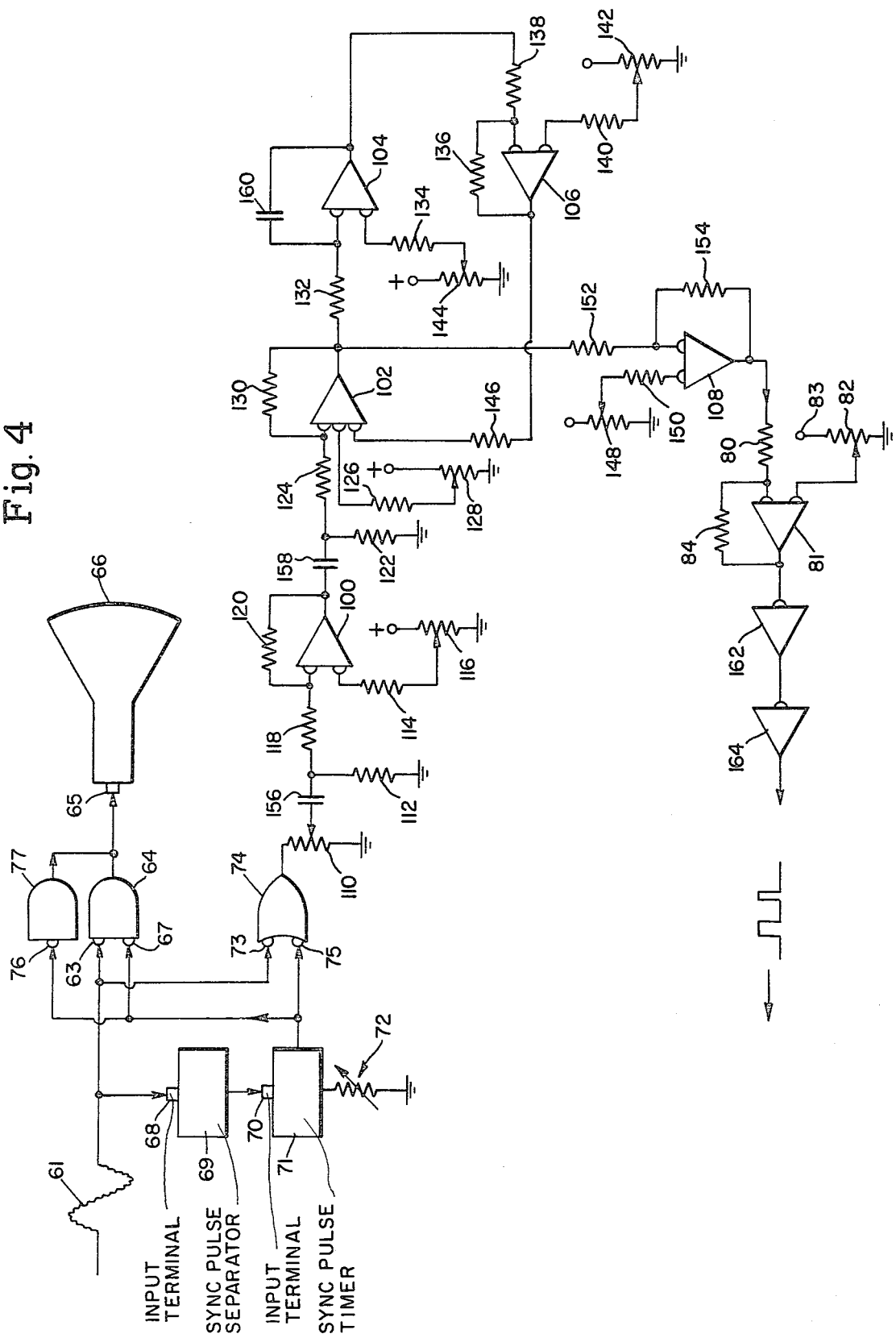
FIG. 4 is a circuit diagram of the video analyzer, filter used for removing interference signals, and signal comparator.

The video signal from the television camera 16 may be processed and fed into a digital computer to obtain numerical data. A system for such processing is shown in FIG. 4. The video signal is fed to a video analyzer system 60 where it is displayed on a kinescope monitor 66 while selected parts thereof are simultaneously displayed as a line on the kinescope monitor and preferably fed through a filter to an analog signal comparator system. The output signal from video analyzer system 60, having the simulated waveform illustrated in FIG. 4, is filtered and shaped, generally into the form illustrated, so that it is suitable for feeding into a digital computer (not shown). Pulses from the analog signal comparator system are fed to the digital computer which is programmed to arrange them into useful information using count and pulse widths.

It is preferred in most instances to display the video signal on a kinescope monitor 66. Obviously, however, such display is not necessary for processing the video signal to be fed into a digital computer.

The video signal produced by a standard television camera is an electrical signal characterized by a content of electrical alternating wave frequencies ranging from 30 hertz to as high as 35 megahertz. The amplitude of the waves contained within this band of frequencies defines the brightness of the portion of the televison picture associated with the wave. The frequency defines the size of the picture element associated with the wave portion. High amplitudes represent bright picture elements. High frequencies represent small picture elements.

In digital analysis of a picture, the brightness of the image can be reduced to a binary number in which presence of a signal above a minimum level represents a shadow being present, and lack of such a shadow is represented by a signal which falls below the minimum level. In digital logic parlance, presence of a shadow is defined as a 1. Absence of a shadow is defined as a zero. Simplification of the signal description relative to amplitude conditions to a 1 or zero state makes possible the elimination of complicated electronic circuits capable of handling the wide range of signals which are required to synthesize a complex wave form which would normally describe the presence of a shadow.

The operation of the video analyzer system 60, which is designed to convert the video signal received from a standard television camera into a waveform suitable for being introduced into an limiting circuit 79, may be described as follows.

The video signal 61 from the television camera 16 is applied to the first input terminal 63 of a NOR gate 64. The output of the NOR gate is electrically connected to the input terminal 65 of a kinescope monitor system 66. Thus, so long as no control signal is present at the second input terminal 67 of the NOR gate 64, the video signal 61 applied to terminal 63 is passed through the gate to and is displayed on the kinescope monitor 66.

The video signal 61 from the television camera is also simultaneously applied to the input terminal 68 of a suitable horizontal synchronization pulse separator circuit 69. Each horizontal synchronization pulse contained in the video signal 61 is detected by this circuit and, after being suitably reshaped, is applied as a trigger pulse from the output of circuit 69 to the input terminal 70 of a synchronization pulse timer circuit 71. Circuits 69 and 71 may be contained in a single unit, if desired.

The trigger pulse from circuit 69 starts the running of the synchronization pulse timer circuit 71, which is designed to produce a single control pulse at its output terminal of a predetermined duration for each trigger pulse received. An adjustable potentiometer 72 is electrically connected to circuit 71 and is used to adjust the point in time when the leading edge of the control pulse appears on the output terminal of the circuit in relationship to the time at which the leading edge of the trigger pulse appeared at the input terminal 70 of the circuit.

The first input terminal 73 of an AND gate 74 is electrically connected directly to the input terminal 63. The second input terminal 75 of the AND gate 74, as well as the second input terminal 67 of NOR gate 64, is electrically connected to the output terminal of the synchronization pulse timer circuit 71. Preferably, amplifier circuit 77 is used in connection with this invention. However, amplifier circuit 77 may be omitted if desired. If used, the input terminal 76 of an amplifier circuit 77 is also electrically connected to the output terminal of circuit 71.

As the leading edge of the control pulse from the synchronization pulse timer circuit 71 appears on the second input terminal 67 of NOR gate 64, it turns this gate off thereby removing the video signal from the kinescope monitor circuit 66. Simultaneously, the leading edge of the control pulse appears at the input terminal 76 of the amplifier circuit 77 wherein it is processed and applied through the output terminal of this circuit to the input terminal 65 of the kinescope monitor 66. This results in part of a vertical line being produced on the face of the kinescope which is the width of the control pulse and is positioned on the kinescope face in accordance with when the control pulse is generated in reference to the horizontal synchronization pulse. Once the trailing edge of the control pulse passes, the NOR gate 64 is turned back on and the output from amplifier circuit 76 terminates.

When the leading edge of the control pulse from the synchronization pulse timer circuit 71 is applied to the second input terminal 75 of AND gate 74, the gate is turned on thereby passing the video signal from input terminal 63 to the output terminal of the video analyzer system 60. This passing of the video signal through AND gate 74 will continue so long as the control pulse is present at input terminal 75.

As will be appreciated, through the use of this video analyzer system, the face of the kinescope monitor circuit will display the picture being picked up by the television camera plus a vertical line that represents the position and portion of the video signal that is being passed through AND gate 74 to the analog signal comparator. Thus, a line selection is provided wherein one sample of a predetermined width is taken at a preselected point in each horizontal sweep line of the kinescope. This sample, combined with the others so taken, forms a vertical line or row. The preselected point at which the samples are taken, and therefore the position of the vertical line formed by the samples, can be electrically positioned to any point on the kinescope face by adjusting potentiometer 72.

Video analyzer systems, as described generally above, are commercially available. For example, Video Analyzer 301 and Video Analyzer 302 are available from Colorado Video, Incorporated, of Boulder, Colo.

In the processing of television signals derived from a monitor system, signals may be produced by the presence of areas of light and dark due to the shadowing illumination produced by a light source positioned to reveal the presence of crimp folds by low angle illumination. As a result of poor illumination uniformity, areas of light and dark may be present in the picture area, and these areas produce signals which add algebraically to the desired signal produced by the crimp to produce excursions in signal level which are frequently greater than the amplitude of the signal produced by the crimp pattern. The excessively strong signal may overpower any threshold devices which may be inserted into the signal processing chain to establish a baseline for the normal alternating wave pattern produced by a crimp pattern. The wide excursions caused by unwanted signals will drive a composite television (consisting of video and synchronization pulses) signal past the threshold level, resulting in a condition where the desired signal is either above or below the threshold level and unavailable for analysis since the function of the threshold device is to clip or limit the normal alternating wave form so that it possesses a square wave or pulse form after processing. The net effect of the additional excursion in the wave form is to push the desired information past the threshold limits, thereby wiping out the desired signal information.

The video signal may be processed to remove the synchronization signals, then to remove the interfering low frequency signals because of uneven illumination of the picture and uneven response from the television camera sensitive camera tube.

The filtering circuit comprises means for eliminating certain signals which interfere with the useful signals. These interference signals include (a) synchronizing signals which have a polarity such that they increase in amplitude from a zero signal level in a negative polarity, opposite that of the useful signals, and (b) signals having a relatively low frequency compared to the useful signals which are usually caused by shadows larger than the light and shadowed strips representing surface irregularities. The low frequency signals are characterized by having a waveform which rarely reverses in polarity over the time period described in a single television picture field in a system having a 60 Hz field rate.

The interfering synchronizing signals, i.e., those which synchronize the television picture as it is scanned by both the television camera and the television monitor, may conveniently be removed by passing the composite signal through an operational amplifier 100 biased to cut off, or fail to amplify the negative signals. Amplifier 100 thus removes the synchronization signal from the composite signal, leaving only the useful signal and any interference (relatively low frequency) signals which may be present. These remaining signals are fed through capacitor 158 to remove any DC signals which may be present, and into an operational amplifier 102 which is designed to algebraically sum these remaining signals with the integrated signal output from this amplifier. The output from amplifier 102 is fed into amplifier 104, which is arranged to integrate the signal fed into it as a function of time. The output of amplifier 104 is then fed through amplifier 106 which has unity amplification, but has 180° phase or polarity reversal relationship with the signal from amplifier 104. The output of amplifier 106 is then fed back into another input of amplifier 102. The signal fed back into amplifier 102 is therefore polarized oppositely to the signal fed to the other input. The output from amplifier 102 thus consists of the difference between the integrated signal output of amplifier 102 and the inteference and useful signals which are fed into the other input of amplifier 102.

If amplifier 104 should be arranged such that its integration rate was short enough to complete the integration of each signal excursion passed to its input, the output of amplifier 104 would follow these excursions exactly, with polarity reversal, and the polarity-corrected input to amplifier 102 via amplifier 106 would add with the input to amplifier 102 from the initial signal source to produce an output of zero. Amplifier 104, however, is designed to have an integration rate which is too slow to follow the excursions of the useful signal, but fast enough to follow the excursions of the interference signals, which normally have excursions with a rate of change of approximately one-fourth to one-tenth of the useful signal. This results in the rapidly varying excursions of the useful signal not being following by the integration of amplifier 104, and the output of this amplifier fails to contain the integral of the useful signal. When this integrated signal output is fed to amplifier 102, the algebraic sum of it and the composite of useful and interference signals leaves the useful signal with an amplitude above zero, while the interference signal terms are near zero. The useful signal term is therefore present in the output of amplifier 102 in considerable strength, while the interference signals have been reduced to a point where they are insignificant by the amplifying effect of the integrating amplifier 104. The useful signal is raised above the interference signal so that by minimal amplification through amplifier 108, the useful signal may be employed for analysis.

The useful signal is then directed from the output of amplifier 108 to the input of an operational amplifier 81 used as a voltage comparitor. The signal is compared with a steady DC signal by an algebraic summing process. Amplifier 81 is designed to produce its maximum output signal if the useful signal is greater than the DC signal. If the output signal is less, the amplifier produces no signal output.

The video signal taken from the video analyzer system, representing a slow-scan video signal showing the luminosity of points sampled along a vertical line which intersects each of the scanning lines of the video picture, is fed through the filter described above and into the analog signal comparator circuit. A typical example of such a circuit is shown although other circuitry for accomplishing this function will be apparent to those skilled in the art. The video signal is fed through a resistor 80 to an analog signal comparator 81. The comparator (type LM 311 manufactured by Intersil Corporation) delivers a digitized signal only if the introduced signal exceeds the level of a threshold voltage taken from a power source, such as shown by variable potentiometer 82. The excitation of the potentiometer is taken from a suitable direct current power supply 83 which also serves as excitation for the comparitor circuit. A feedback loop including a resistor 84 connects the output of comparitor 81 to threshold input signal. This resistor defines the sensitivity of the comparitor to signal differences.

When the leading edge of a pulse rises above the threshold voltage setting, the analog signal comparator circuit is turned on and produces the leading edge of an output pulse. When the trailing edge of the pulse 87 falls below the threshold voltage setting, the analog signal comparator circuit is turned off thereby terminating the pulse. This pulse generating process is repeated with each video signal pulse that exceeds the predetermined setting of the threshold voltage level.

As will be apparent, video input pulses that do not exceed this threshold voltage level will not activate or turn on the analog signal comparator circuit and thus will not appear in the output pulse train.

Suitable feedback resistors 84, 120, 130, 136 and 154 are provided at amplifiers 108, 100, 102, 106 and 81 respectively. Capacitor 160 is provided at amplifier 104 to set the integration rate to correspond with a rate of 30 frames per second and 525 lines interlaced scanning. Amplifier 164 serves as a polarity inverter for the signal coming from amplifier 162.

Examples of typical specifications for electrical components shown in the drawing are as follows:

| Capacitor | Size |
|---|---|
| 156 | 0.5 μf |
| 158 | 0.5 μf |
| 160 | 0.0005 μf |
| Resistor | Size |
| 80 | 1K |
| 82 | 1K |
| 84 | 3.9K |
| 114 | 10K |
| 116 | 1K |
| 120 | 20K |
| 122 | 10K |
| 124 | 10K |
| 130 | 10K |
| 132 | 800 ohm |
| 134 | 500 ohm |
| 136 | 10K |
| 138 | 10K |
| 140 | 10K |
| 142 | 1K |
| 144 | 1K |
| 146 | 10K |
| 148 | 1K |
| 150 | 100K |
| 152 | 10K |
| 154 | 100K |
| Amplifiers | Type |
| 81 | LM 311 product of Signetics, Inc. |
| 100 | RCA 3130 |
| 102 | RCA 3130 |
| 104 | RCA 3130 |
| 106 | RCA 3130 |
| 108 | RCA 3130 |
| 162 | transistor-transistor-logic 7404 series of integrated circuits |
| 164 | transistor-transistor-logic 7404 series of integrated circuits |

In the table, K represents 1000 ohms, and μf represents microfarads.

Pulses from the analog signal comparator circuit are then fed in a conventional manner to a digital computer, which uses the count and width of the pulses to provide numerical information on bodies contained within a mass moving through the television camera's field of view.

The square wave signal produced as described above, or by other means such as amplification in a limiter amplifier to the point where wave squaring is effected, or by shaping in a diode clipping circuit, is well suited for introduction to the input system of conventional electronic digital counters such as, for example, the series manufactured by the Hewlett-Packard Company and marketed under the series number 5300. The square wave produced by the analog signal comparitor is introduced to the counter. The counter registers one count of each square wave introduced to it. The total count over a count of 4000 sample scans is found to agree with that produced by a digital computer supplied with the same signal.

In addition to the simplified means of producing a signal suitable for introduction to a computer, an analog-to-digital converter system which translates the gray scale of the video image into a digital code and stores it in the computer memory may be used. Once in memory, the computer is programmed to accept digital codes representing a level above the threshold established, and to reject those codes representing levels below the threshold. A count of the acceptable codes is made and the time during which the code is received recorded. One count is recorded for each time the code is received. The count is distributed in the record according to the time duration of the code received. A single video frame representing 1/30 second of time is digitized by the analog to digital converter and entered into the computer memory.

This invention will be further illustrated by the following example although it will be understood that this example is included merely for purposes of illustration and is not intended to limit the scope of the invention.

EXAMPLE

A closed circuit television camera is installed to observe a running tow band of polyester fiber having a width of approximately 12 inches and a thickness of approximately 1/16-inch. Crimps are placed transverse to the running axis of this tow band by means of a crimping device. Illumination is provided by means of a stroboscopic light source synchronized to the field rate of the camera. The duration of the light pulse is adjusted to be in the order of one microsecond. The pulse of light is arranged to flash at the beginning of the sweeping out of a single field. Thus the image which falls upon the camera tube target is imposed in one microsecond and is retained during the time it takes for the sweeping of the electron beam to pick up the electronic image and translate it to a video signal. Since the tow band is running at a rate of about 400 meters per minute, movement of the two band image on the camera tube during the time the flash of light lasted is minimized and the distortion due to movement of the image on the camera tube target is minimized. If the flash of light lasts longer, the result is a smearing of the image on the camera tube target and distortion of the video image.

The camera is adjusted to provide a high-contrast picture, so that the image of the crimps in the two band (made to stand out in light and shadow because of the low angle of lighting used) is made even more sharply contrasted with the shadowed portions being extremely dark, and the light portions equally light with respect to the dark part of the picture. This extreme contrast results in a video signal amplitude which had a wide excursion.

The signal due to uneven illumination of the tow band, and the signal due to uneven response from the television camera tube are added together in the output of the television camera. These signals are in addition to the television signal produced by the camera as a result of its photographing the two band formed of crimped fiber. These signals add to the desired signal produced by scanning the crimped tow, to produce a signal which when viewed on an oscilloscope appear to have the useful signal riding the crests of the signal waves produced by uneven illumination and uneven camera tube response.

For the purpose of extracting a signal more adapted to the frequency responsive characteristics of the counter and computer system which measure the number of pulses (crimps) in a given length of tow band. Video Analyzer 302 manufactured by the Colorado Video Company, Incorporated, is installed. The video signal from the television camera is directed to the input of this apparatus where it is processed to produce a signal representing the luminance at the intersection of each scanning line and an arbitrary vertical line drawn through the picture. This arbitrary line is positioned to fall in an area of picture representing the tow band where crimp count is considered important. The camera is oriented to cause the movement of the tow band to run from the top of the television picture to the bottom. This results in the crimp pattern running across the longer axis of the picture so that waves of crimp move from the top of the picture to the bottom. The vertical line thus intersects the waves of crimp, and the luminance at the points where it intersects the crimp is translated into an AC wave describing the brightness and darkness caused in the picture by the interception of the crest and valley structure of the crimp of the parallel rays of light emanating from the stroboscopic light source (which is arranged to illuminate the tow band with a small angle between the axis of the light rays and the plane of the tow band).

The signal processing system is connected into the signal train to receive the slow scan video output of the video analyzer. Because uneven illumination exists over the area of the picture traversed by the line, the slow scan video signal is contaminated with undesirable signals because of lighting imperfections. There are also imperfections because of the uneven response of the camera tube target.

Examination of the slow scan video signal without processing shows that the useful signal is unacceptable to the comparitor wave shaper used to prepare the pulses generated by the crimp pattern for acceptance by the counter and computer system. When this comparitor is fed by this contaminated signal it produces an output indicating that there were large crimps which are fed in number. Visual examination of the events using an oscilloscope shows that the large signal amplitude excursions are forcing the desired signal into amplitudes where the signal is eliminated by the thresholding apparatus.

Upon installation of the signal processing system, visual observation of the signal fails to reveal any signal other than that due to the crimp pattern. When this signal is presented to the comparitor, a true count of crimp and a true measure of crimp period is produced by the counter and computer system.

The system is first tested with tow which has been mechanically determined to contain 10 crimps per inch. The counter system indicates that this was the number of crimps present in the tow band. For this measurement the tow band was moving by the television camera station at 400 meter per minute.

In the Example, typical specifications are as follows:

Frequency range of useful signal—300 Hz–10 MHz
Frequency range of undesirable signal—30 Hz–300 Hz
Rate of scanning by TV camera—30 frames/sec. 525 line interlaced.

The invention has been described in detail with particular reference to certain preferred embodiments thereof, but it will be understood that variations and modifications can be effected within the spirit and scope of the invention.

I claim:

1. Apparatus for determining information relative to surface irregularities in elongated material comprising
   (A) a television camera positioned such that its field of view is a portion of the elongated material,
   (B) light means positioned adjacent the path of said elongated material such as to illuminate said elongated material at an angle to cause a pattern of light and shadowed areas,
   (C) means synchronizing said television camera and light means such that a television frame is initiated during an illumination, and a video signal is formed of the illuminated material,
   (D) means for filtering low frequency signal components from the composite video signal caused by different illumination intensities on relatively large areas of said elongated material, and
   (E) means for using the digitized signal as a source of information in the inspection of said elongated material.

2. Apparatus according to claim 1 wherein said means for filtering low frequency signal components comprises:
   (a) first amplifier means;
   (b) means for feeding said composite video signal to an input terminal of said first amplifier means;
   (c) integrating circuit means adopted to integrate an input signal as a function of time, the integrating rate being too slow to follow the high frequency elements of said composite video signal component above about 300 Hz, but sufficiently fast to follow the low frequency elements thereof,
   (d) means for electrically connecting the output from said first amplifier means to the input terminal of said integrating circuit means;
   (e) means for inverting the output signal from said integrating circuit means, and
   (f) means connecting said inverted output signal to said input terminal of said first amplifier means whereby the output from said first amplifier is the difference between the integrated signal output of said first amplifier and the combined high and low frequency elements of said composite video signal.

3. Apparatus according to claim 2 wherein said integrating circuit means includes an amplifier and capacitor bypass circuit.

4. Apparatus according to claim 1 wherein said means for filtering low frequency signal components comprises:
   (a) a first amplifier,
   (b) means for feeding the composite signal into an input terminal of said first amplifier,
   (c) means electrically connecting the output terminal of said first amplifier to the input terminal of a second amplifier,
   (d) a capacitor circuit connecting the input and output terminals of said second amplifier, said capacitor circuit and said second amplifier being operable to integrate the input signal to said second amplifier as a function of time, the integration rate being too slow to follow the high frequency elements but sufficiently fast to follow the low frequency elements, (e) means electrically connecting said output terminal of said second amplifier to the input terminal of a third amplifier having unity amplification and polarity reversal with respect to said second amplifier, (f) means electrically connecting the output terminal of said third amplifier to an input terminal of said first amplifier, whereby the output from said first amplifier is the difference between the integrated signal output of said first amplifier and the combined high and low frequency components, and (g) means electrically connecting the output terminal of said first amplifier with the input terminal of a fourth amplifier, whereby only the high frequency elements are amplified.

5. Apparatus for obtaining information relative to surface irregularities in elongated material advancing along a predetermined path comprising
(A) a television camera positioned such that its field of view is a portion of the advancing elongated material,
(B) a stroboscopic light positioned adjacent the path of said elongated material such as to illuminate said elongated material at an angle to cause a pattern of light and shadowed areas,
(C) means synchronizing said television camera and stroboscopic light such that a television frame is initiated during an illumination, and a video signal is formed of the illuminated material,
(D) means for filtering low frequency signal components from the composite video signal caused by different illumination intensities on relatively large areas of said elongated material comprising
  (a) a first amplifier
  (b) means for feeding the composite signal into an input terminal of said first amplifier,
  (c) means electrically connecting the output terminal of said first amplifier to the input terminal of a second amplifier,
  (d) a capacitor circuit connecting the input and output terminals of said second amplifier, said capacitor circuit and said second amplifier being operable to integrate the input signal to said second amplifier as a function of time, the integration rate being too slow to follow the high frequency elements but sufficiently fast to follow the low frequency elements,
  (e) means electrically connecting said output terminal of said second amplifier to the input terminal of a third amplifier having unity amplification and polarity reversal with respect to said second amplifier,
  (f) means electrically connecting the output terminal of said third amplifier to an input terminal of said first amplifier, whereby the output from said first amplifier is the difference between the integrated signal output of said first amplifier and the combined high and low frequency components, and
  (g) means electrically connecting the output terminal of said first amplifier with the input terminal of a fourth amplifier, whereby only the high frequency elements are amplified, and
(E) means for using the digitized signal as a source of information in the inspection of said elongated material.

6. Apparatus according to claim 5 wherein at least the portion of the path of said elongated material within the field of view of said television camera is substantially linear.

7. Apparatus according to claim 5 wherein the elongated material is crimped tow and the stroboscopic light source provides a beam of light collimated in at least one direction and is positioned such that the rays thereof are substantially parallel to one slope of the crimped tow at the maximum anticipated crimp angle.

8. Method of obtaining information relative to surface irregularities in elongated material advancing along a predetermined path comprising
(A) positioning a television camera such that its field of view is a portion of the advancing elongated material,
(B) positioning a stroboscopic light adjacent the path of said elongated material such as to illuminate said elongated material at an angle to cause a pattern of light and shadowed areas,
(C) synchronizing said television camera and stroboscopic light such that a television frame is initiated during an illumination, and a video signal is formed to the illuminated material,
(D) filtering low frequency signal components from the composite video signal caused by different illumination intensities on relatively large areas of said elongated material by apparatus comprising
  (a) a first amplifier,
  (b) means for feeding the composite signal into an input terminal of said first amplifier,
  (c) means electrically connecting the output terminal of said first amplifier to the input terminal of a second amplifier,
  (d) a capacitor circuit connecting the input and output terminals of said second amplifier, said capacitor circuit and said second amplifier being operable to integrate the input signal to said second amplifier as a function of time, the integration rate being too slow to follow the high frequency elements but sufficiently fast to follow the low frequency elements,
  (e) means electrically connecting said output terminal of said second amplifier to the input terminal of a third amplifier having unity amplification and polarity reversal with respect to said second amplifier.
  (f) means electrically connecting the output terminal of said third amplifier to an input terminal of said first amplifier, whereby the output from said first amplifier is the difference between the integrated signal output of said first amplifier and the combined high and low frequency components, and
  (g) means electrically connecting the output terminal of said first amplifier with the input terminal of a fourth amplifier, whereby only the high frequency elements are amplified, and
(E) using the digitized signal as a source of information in the inspection of said elongated material.

9. Method according to claim 8 which includes, prior to filtering, the step of electrically applying the video signal from the television camera to the input of separator circuit means which is adapted to produce a control pulse on its output terminal of predetermined duration for each horizontal synchronization pulse contained in said video signal, and electrically applying the video signal and the control pulse from the separator circuit means to separate into terminals of gate means adapted to pass said video signal through to its output terminal whenever said control pulse is applied to said second input terminal.

10. Method according to claim 9 which includes the steps of
 (a) electrically applying the output signal from the filtering means to comparator means for converting all pulses of greater than a predetermined amplitude contained within said passed video signal into a digitized signal, and
 (b) using the digitized signal as a source of information in the inspection of said elongated material.

* * * * *